US007223848B2

(12) United States Patent
Coffman et al.

(10) Patent No.: US 7,223,848 B2
(45) Date of Patent: May 29, 2007

(54) METHODS FOR PURIFYING FC-CONTAINING PROTEINS

(75) Inventors: Jonathan L. Coffman, Haverhill, MA (US); William B. Foster, Chelmsford, MA (US); Shujun Sun, Brentwood, NH (US)

(73) Assignee: Genetics Institute, LLC, Cambridge, MA (US)

( * ) Notice: Subject to any disclaimer, the term of this patent is extended or adjusted under 35 U.S.C. 154(b) by 431 days.

(21) Appl. No.: 10/163,853

(22) Filed: Jun. 5, 2002

(65) Prior Publication Data
US 2003/0050450 A1    Mar. 13, 2003

Related U.S. Application Data

(60) Provisional application No. 60/296,402, filed on Jun. 5, 2001.

(51) Int. Cl.
*C07K 1/18* (2006.01)
*C07K 1/20* (2006.01)
*C07K 1/22* (2006.01)

(52) U.S. Cl. ............... 530/413; 436/828; 530/415; 530/416; 530/417

(58) Field of Classification Search ............ 530/413, 530/415, 416, 417; 436/828
See application file for complete search history.

(56) References Cited

U.S. PATENT DOCUMENTS

| | | | | |
|---|---|---|---|---|
| 5,115,101 A | * | 5/1992 | Bloom et al. | 530/388.25 |
| 5,429,746 A | | 7/1995 | Shadle et al. | 210/635 |
| 5,644,036 A | * | 7/1997 | Ramage et al. | 530/412 |
| 5,726,293 A | * | 3/1998 | Seed | 530/413 |
| 5,827,817 A | | 10/1998 | Larsen et al. | 514/2 |
| 5,852,175 A | | 12/1998 | Cummings et al. | 530/388.73 |
| 6,005,075 A | | 12/1999 | Ettlin et al. | 530/351 |
| 6,005,081 A | | 12/1999 | Burton et al. | 530/399 |
| 6,005,082 A | | 12/1999 | Smeds | 530/417 |
| 6,008,036 A | | 12/1999 | Fanget et al. | 435/239 |
| 6,008,328 A | | 12/1999 | Hsu et al. | 530/412 |
| 6,028,191 A | | 2/2000 | Nardella et al. | 536/124 |
| 6,127,526 A | * | 10/2000 | Blank | 530/413 |
| 6,740,736 B2 | | 5/2004 | McCreath | 530/382 |

FOREIGN PATENT DOCUMENTS

| | | |
|---|---|---|
| EP | 0345549 A | 12/1989 |
| WO | WO 95/22389 A | 8/1995 |
| WO | WO 98/08949 A1 | 5/1998 |
| WO | WO 98/23645 A | 6/1998 |
| WO | WO 00/25808 A1 | 5/2000 |
| WO | WO 00/43781 A2 | 7/2000 |
| WO | WO 01/72769 * | 10/2001 |

OTHER PUBLICATIONS

Wong et al. (1995) "The Guanylyl Cyclase-A Receptor Transduces an Atrial Natriuretic Peptide/ATP Activation Signal in the Absence of the Other Proteins", J. Biol. Chem. 270:30818-22.

Simpson et al. (2004) "The Strongest Link in the Protein Purification Chain", Promega Notes 86:11-14, 11.

"Affinity Chromatography" definition, available at http://en.wikipedia.org/), printed Jan. 31, 2006.

Shapiro (1987) "Elimination of the detection of an artefactual 65 kDa keratin band from immunoblots", J. Immunol. Methods 102:143-46.

Davis et al. (1994) "Basic Methods of Protein Analysis" in Basic Methods in Molecular Biology, 2nd Ed., p. 669-678, Appleton and Lange, Norwalk, CT.

Khuntirat and Lucher (1990) "A microscale analytical batch chromatographic method for detecting soluble viral DNA-binding proteins in crude extracts", J. Virol. Methods. 29:97-103.

Li, F. et al., "Visualization of P-selectin glycoprotein ligand-1 as a highly extended molecule and mapping of protein epitopes for monoclonal antibodies," J. Biol. Chem. (1996) Mar. 15; 271(11):6342-48.

Lottspeich, F. (ed.) "Bioanalytik," (1998) Spektrum Akademischer Verlag, Heidelberg, Berlin pp. 208-209 [and English translation thereof].

Moore, K.L. et al., "The P-selectin glycoprotein ligand from human neutrophils displays sialylated, fucosylated, O-linked poly-N-acetyllactosamine," J. Biol. Chem. (1994) Sep. 16; 269(37):23318-27.

Balint et al., "Tumoricidal Response Following Perfusion Over Immobilized Protein A: Identification of Immunoglobulin Oligomers In Serum After Perfusion and Their Partial Characterization," Cancer Research, vol. 44, No. 2, pp. 734-743 (Feb. 1984).

Hoedemaeker et al., "A Single Chain Fv Fragment of P-Glycoprotein-Specific Monoclonal Antibody C219. Design, Expression, and Crystal Structure At 2.4 Å Resolution," (1997) J. Biol. Chem. 272:29784-89.

Casey et al. "Purification of Bacterially Expressed Single Chain Fv Antibodies for Clinical Applications Using Metal Chelate Chromatography," (1995) J. Immunol. Methods 179:105-116.

* cited by examiner

*Primary Examiner*—David A. Saunders
(74) *Attorney, Agent, or Firm*—Fitzpatrick, Cella, Harper & Scinto

(57) ABSTRACT

The present invention provides a process for dissociating Fc-containing molecules from complexes of Protein A/Fc-containing molecules or mixtures containing Fc-containing molecules and Protein A. The association, e.g., by hydrophobic interactions, between the Fc-containing molecules and Protein A can be reduced or inhibited by raising the pH of dissociation. The pH of dissociation can be raised by addition of agents capable of inhibiting hydrophobic interactions, including buffers containing arginine and/or ethylene glycol, to the mixture, either prior to adding the mixture to the column chromatography substrate, after adding the mixture to the column chromatography substrate, or both prior to and after adding the mixture to the column chromatography substrate. Separation of Fc-containing molecules from Protein A can be performed on a number of different column chromatographic substrates, including column chromatographic substrates contained in Q columns (Q column chromatography substrate), HIC columns (hydrophobic interaction column chromatography substrate), and IMAC columns (metal chelate column chromatography substrate).

21 Claims, No Drawings

SEQUENCE LISTING

```
<160> NUMBER OF SEQ ID NOS: 1

<210> SEQ ID NO 1
<211> LENGTH: 402
<212> TYPE: PRT
<213> ORGANISM: homo sapiens

<400> SEQUENCE: 1

Met Pro Leu Gln Leu Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
            20                  25                  30

Gly Pro Leu Leu Ala Arg Asp Arg Arg Gln Ala Thr Glu Tyr Glu Tyr
        35                  40                  45

Leu Asp Tyr Asp Phe Leu Pro Glu Thr Glu Pro Pro Glu Met Leu Arg
    50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Arg Ser Thr Gly Leu Asp Ala Gly
                85                  90                  95

Gly Ala Val Thr Glu Leu Thr Thr Glu Leu Ala Asn Met Gly Asn Leu
            100                 105                 110

Ser Thr Asp Ser Ala Ala Met Glu Ile Gln Thr Thr Gln Pro Ala Ala
        115                 120                 125
```

-continued

```
Thr Glu Ala Gln Thr Thr Pro Leu Ala Ala Thr Glu Ala Gln Thr Thr
        130                 135                 140

Arg Leu Thr Ala Thr Glu Ala Gln Thr Thr Pro Leu Ala Ala Thr Glu
145                 150                 155                 160

Ala Gln Thr Thr Pro Pro Ala Ala Thr Glu Ala Gln Thr Thr Gln Pro
                165                 170                 175

Thr Gly Leu Glu Ala Gln Thr Thr Ala Pro Ala Ala Met Glu Ala Gln
                180                 185                 190

Thr Thr Ala Pro Ala Ala Met Glu Ala Gln Thr Thr Pro Pro Ala Ala
        195                 200                 205

Met Glu Ala Gln Thr Thr Gln Thr Thr Ala Met Glu Ala Gln Thr Thr
    210                 215                 220

Ala Pro Glu Ala Thr Glu Ala Gln Thr Thr Gln Pro Thr Ala Thr Glu
225                 230                 235                 240

Ala Gln Thr Thr Pro Leu Ala Ala Met Glu Ala Leu Ser Thr Glu Pro
                245                 250                 255

Ser Ala Thr Glu Ala Leu Ser Met Glu Pro Thr Thr Lys Arg Gly Leu
                260                 265                 270

Phe Ile Pro Phe Ser Val Ser Ser Val Thr His Lys Gly Ile Pro Met
            275                 280                 285

Ala Ala Ser Asn Leu Ser Val Asn Tyr Pro Val Gly Ala Pro Asp His
        290                 295                 300

Ile Ser Val Lys Gln Cys Leu Leu Ala Ile Leu Ile Leu Ala Leu Val
305                 310                 315                 320

Ala Thr Ile Phe Phe Val Cys Thr Val Val Leu Ala Val Arg Leu Ser
                325                 330                 335

Arg Lys Gly His Met Tyr Pro Val Arg Asn Tyr Ser Pro Thr Glu Met
                340                 345                 350

Val Cys Ile Ser Ser Leu Leu Pro Asp Gly Gly Glu Gly Pro Ser Ala
        355                 360                 365

Thr Ala Asn Gly Gly Leu Ser Lys Ala Lys Ser Pro Gly Leu Thr Pro
    370                 375                 380

Glu Pro Arg Glu Asp Arg Glu Gly Asp Asp Leu Thr Leu His Ser Phe
385                 390                 395                 400

Leu Pro
```

METHODS FOR PURIFYING FC-CONTAINING PROTEINS

RELATED APPLICATIONS

This application claims the benefit of U.S. provisional patent application No. 60/296,402, filed on Jun. 5, 2001, the contents of which is hereby incorporated by reference in its entirety.

BACKGROUND OF THE INVENTION

1. Field of the Invention

The present invention is directed to methods for dissociating Fc containing molecules from complexes of Protein A/Fc containing molecules in mixtures.

2. Related Background Art

Purification of target proteins is often encumbered by poor DNA removal due to DNA/protein interactions. DNA/protein interactions are more problematic in the purification of highly anionic target proteins, e.g., sulfated proteins. Purification of proteins, e.g., proteins containing immunoglobulin domains, is also often difficult based on the low pH of dissociation required to separate Fc containing molecules from Protein A. The identification of methods useful in removing DNA from target proteins and the identification of methods for removing Protein A from target proteins would be of great benefit in the purification of various proteins.

International Publication No. WO 01/72769 describes methods for isolating and purifying highly anionic target proteins and target proteins comprising immunoglobulin domains, for example, sulfated proteins. Anionic proteins are proteins which have a net negative charge. Sulfated proteins are proteins in which the net negative charge is due to at least about one (1) sulfated residue. Sulfation of a target protein refers to the substitution of at least one hydroxyl group (—OH) with —SO$_4$H on or between amino acid(s) contained within the target protein. In a preferred embodiment, the sulfated protein has at least about one (1) sulfate group. Sulfated proteins containing at least about two (2), three (3), four (4), five (5), six (6) or more sulfate groups are also encompassed by the present methods, e.g., six sulfate groups on the N-terminal tyrosines as embodied in PSGL-1 (P-Selectin Glycoprotein Ligand-1).

In particular, International Publication No. WO 01/72769 discloses, in one aspect, a method for purifying highly anionic target proteins comprising the steps of ion exchange chromatography under appropriate conditions for the purification of the target proteins. As an example, the disclosed method provides for (1) contacting the sample with a substrate capable of reversibly binding charged molecules whereby the target proteins bind to the substrate, (2) washing the substrate with a first wash solution under appropriate conditions whereby a plurality of proteinaceous and non-proteinaceous impurities in the sample either do not bind or are washed off the substrate while the highly anionic target proteins remain bound, (3) eluting the sample with a first elution solution wherein the first elution solution comprises a salt solution at a high molar concentration, and (4) collecting the eluted sample containing the purified anionic target proteins.

In one embodiment, it is disclosed that the pH of the first wash solution is about 4.0 to 8.0. In another embodiment, it is disclosed that the pH of the first wash solution is about 6.5.

In a preferred embodiment, it is disclosed that the highly anionic target protein is a sulfated protein and the impurities include a sulfated form of the target protein.

International Publication No. WO 01/72769 also discloses that the eluted sample from the ion exchange chromatography purification which contains the purified target proteins can be further purified. This further purification, for example, comprises the steps of hydrophobic interaction and/or metal chelate chromatography under appropriate conditions for the purification of the highly anionic target proteins. For example, this further purification provides for the steps of (1) passing the eluted sample containing the target proteins through a metal chelate chromatography column or a hydrophobic interaction chromatography column whereby the eluted sample is captured on the column, (2) washing the column with a second wash solution under appropriate conditions whereby DNA/histone complexes contained in the sample are dissociated, (3) eluting the sample with a second elution solution, and (4) collecting the eluted sample containing the purified highly anionic target proteins.

In one disclosed embodiment, the second wash solution comprises a high salt concentration and the second elution solution comprises a lower salt concentration than the second wash solution. For example, under hydrophobic interaction chromatographic conditions, the concentration of the salt in the second wash solution is about 4M, and the concentration of the salt in the second elution solution is about 0.48M. Alternatively, under hydrophobic interaction chromatography the second wash solution is selected from the group consisting of (a) a solution comprising NaCl at about 4M and Tris at about 20 mM and a pH of about 7.4, (b) a solution comprising isopropanol at about 5% and ammonium sulfate at about 1.2M, (c) a solution of ethanol at about 5% and ammonium sulfate at about 1.2M, and (d) a solution of ethanol of about 5% and NaCl at about 4M.

It is further disclosed that under iron chelation chromatographic conditions, for example, the second wash solution comprises a salt concentration of about 2M, and the second elution solution comprises a salt concentration of about 200 mM to 1M. Alternatively, under iron chelation chromatographic conditions, the second wash solution comprises MES at about 40 mM, NaCl at about 2M, and imidazole at about 5 mM, and the second elution solution comprises a solution of MES at about 40 mM, NaCl at about 1M, and imidazole at about 35 mM.

International Publication No. WO 01/72769 discloses that the target proteins have at least about one (1) sulfation(s). Anionic target proteins having at least about two (2), three (3), four (4), five (5), six (6), or more sulfations are also disclosed, e.g., PSGL-1 proteins. Anionic proteins capable of being purified by the disclosed methods can be naturally occurring or recombinant proteins.

Also disclosed in International Publication No. WO 01/72769 is a method for the purification of highly anionic proteins comprising an immunoglobulin domain (e.g., an immunoglobulin Fc domain), for example, a PSGL-Ig fusion protein. This disclosed method comprises the steps of (1) contacting the sample with a substrate capable of binding the Fc portion of the target protein comprising an immunoglobulin domain whereby the target molecules bind to the substrate, (2) washing the substrate with a first wash solution under appropriate conditions to wash away contaminants contained in the sample, (3) eluting the sample with a first elution solution wherein the pH of the first elution solution is low, e.g., about 4.0, preferably about 3.7, and (4) collecting the eluted sample containing the purified anionic target proteins.

It is further disclosed that the eluted sample from the Fc binding substrate which contains the purified highly anionic target proteins comprising an immunoglobulin domain may be further purified. For example, further purification comprises the steps of (1) contacting the eluted sample containing the purified anionic target proteins comprising an immunoglobulin domain with a substrate capable of reversibly binding charged molecules whereby a plurality of proteinaceous and non-proteinaceous impurities in the sample either do not bind or are washed off the substrate while the target proteins remain bound to the substrate, (2) washing the substrate with a second wash solution wherein the pH of the second wash solution is low, e.g., about 4.0, preferably about 3.8, (3) eluting the sample with a second elution solution, and (4) collecting the eluted sample containing the purified anionic target proteins comprising an immunoglobulin domain.

In one aspect, it is disclosed that the target proteins comprising an immunoglobulin domain have at least about one (1) sulfation(s). Immunoglobulins comprising proteins with at least two (2), three (3), four (4), five (5), six (6), or more sulfations are also disclosed by International Publication No. WO 01/2769, e.g., PSGL-Ig.

In a preferred embodiment, the purification methods disclosed provide purified highly anionic target proteins and purified highly anionic proteins comprising an immunoglobulin domain (e.g., PSGL-Ig) at least about 99.9% pure of contaminating proteins.

In another disclosed embodiment, the purification methods of the invention removes at least about 95% or 2.5 $\log_{10}$ removal value (LRV) of the contaminating DNA from the highly anionic target proteins and the highly anionic proteins comprising an immunoglobulin domain.

A method, however, for dissociating Fc containing molecules from complexes of Protein A/Fc containing molecules in mixtures would be highly desirable.

This application is related to prior-filed provisional patent application No. 60/193,351, filed on Mar. 27, 2000, prior-filed U.S. patent application Ser. No. 09/819,157, filed on Mar. 27, 2001 (now U.S. Pat. No. 6,933,370), and prior-filed international application No. PCT/US01/09815, filed Mar. 27, 2001. The entire contents of each of the above-referenced applications are incorporated herein by this reference.

SUMMARY OF THE INVENTION

The present invention provides novel methods for removing Protein A (e.g., rProtein A or rPA) from mixtures containing associated, e.g., by hydrophobic interactions, Protein A and Fc containing molecules, such as, for example, rPSGL-Ig molecules. Raising the pH of dissociation, e.g., higher than about pH 3.7, allows the separation of the Fc containing molecules, such as rPSGL-Ig, from Protein A by passing the mixture through a chromatographic column, including, but not limited to, a Q column, e.g., a Q Sepharose™ Fast Flow (Amersham Pharmacia) column, a hydrophobic interaction chromatography (HIC) column, a metal chelate chromatography (IMAC) column, a hydroxy apatite column, or anion exchange or cation exchange columns, thereby removing the Protein A from the mixture. The pH of dissociation can be raised by addition of arginine and/or any composition or agent which reduces (breaks up) or inhibits (prevents) hydrophobic interactions, including, but not limited to ethylene glycol, propylene glycol, ethanol, propanol, methanol, and the like. A higher pH of dissociation allows the removal of rPA at a more normal pH than dissociation would otherwise occur. Use of a higher pH, e.g., higher than about pH 3.7, also results in less damage, e.g., loss of sulfation or sialation or introduction of Asp-Pro cleavages, to some Fc containing proteins due to lower pH, e.g., pH 3.7.

Previously, Q columns could not be used for dissociation of rPA from Fc containing proteins (other than Fc containing proteins which are highly anionic), because the pH was generally too low to allow binding of the Fc molecule or the rProtein A to the Q column. Raising the pH of dissociation by, for example, use of arginine and/or ethylene glycol, the pH of dissociation is high enough to allow the use of the Q column for Fc containing molecules under dissociation conditions, including those molecules that are not highly anionic.

Also, previously, IMAC columns could not be used under dissociation conditions, e.g., low pH, again because the Fc containing molecule and the rPA would not remain bound to the IMAC under the normally low pH necessary for the dissociation to occur. Through raising the pH of dissociation by, for example, use of ethylene glycol, the Fc containing protein remains bound to the IMAC column, such that the MAC column may be used to remove rProtein A.

A HIC column can also be used for removal of rPA from Fc containing molecules at a more normal pH than dissociation would normally occur through raising the pH of dissociation, e.g., by use of arginine and/or ethylene glycol.

In one aspect, the invention provides a method for dissociating Fc containing molecules from complexes of Protein A/Fc containing molecules in a mixture comprising contacting the mixture with a chromatographic column under pH conditions sufficient to dissociate Fc containing molecules from complexes of Protein A/Fc containing molecules. In one embodiment, the Fc containing molecules are eluted from the chromatographic column such that the Fc containing molecules are substantially free from Protein A. In another embodiment, the pH conditions comprise a pH of less than about 6.0. In a further embodiment, the pH conditions comprise a pH higher than about 3.7. In yet another embodiment, the pH conditions are established by the addition of an agent to said mixture which reduces or inhibits hydrophobic interactions, such as, for example, ethylene glycol. In another embodiment, the pH conditions are established by the addition of arginine to said mixture. In yet another embodiment, the pH conditions are established by the addition of arginine in combination with ethylene glycol.

In a further embodiment, the chromatographic column is a metal chelate chromatography column. In still a further embodiment, the pH conditions are between about 5.0 and about 5.7. Preferably, the pH conditions are about 5.0. In another embodiment, ethylene glycol is added to said mixture. In still another embodiment, the chromatography column is an IMAC column and the column is washed with a buffer containing 50% ethylene glycol, 1M NaCl, and 20 mM Na Acetate, at a pH of about 5.0, thereby dissociating complexes of Protein A/Fc containing molecules.

In another aspect, the invention provides a method for dissociating Fc containing molecules from complexes of Protein A and Fc containing molecules in a mixture comprising contacting the mixture with a hydrophobic interaction chromatography column under pH conditions sufficient to dissociate Fc containing molecules from complexes of Protein A and Fc containing molecules, wherein the column is washed with a buffer containing arginine. In one embodiment, the pH conditions are between about 4.1 and about 4.5. In a preferred embodiment, the pH conditions are about 4.1.

In another embodiment, the chromatographic column is a Q column. In a further embodiment, the pH conditions are between about 5.5 and 5.7. In a preferred embodiment, the pH conditions are about 5.5. In a further embodiment, ethylene glycol is added to the mixture.

In another embodiment, the Fc containing molecule is rPSGL-Ig.

Other features and advantages of the invention will be apparent from the following detailed description and claims.

DETAILED DESCRIPTION OF THE INVENTION

The present invention is based, at least in part, on the discovery of novel methods for purifying highly anionic target proteins and highly anionic proteins comprising an immunoglobulin domain, for example, sulfated proteins (e.g., PSGL-1). Anionic proteins are proteins having a net negative charge. Sulfated proteins are anionic proteins in which the negative charge is due to at least about one, or more preferably, five (5) or more, sulfations, e.g., at least about six (6), sulfations. Sulfations in a target protein refer to the substitution of at least one hydroxyl group (—OH) with —SO$_4$H on or between amino acid(s) contained within the target protein. Sulfations can occur, for example, at the N-terminal tyrosines as embodied in PSGL-1.

The present invention is based, also in part, on the discovery of novel methods for removing Protein A (e.g., rProtein A or rPA) from mixtures containing associated, e.g., by hydrophobic interactions, Protein A and Fc containing molecules, such as, for example, rPSGL-Ig molecules. Raising the pH of dissociation, e.g., higher than about pH 3.7, allows the separation of the Fc containing molecules, such as rPSGL-1g, from Protein A by passing the mixture through a chromatographic column, including, but not limited to, a Q column, e.g., a Q Sepharose™ Fast Flow (Amersham Pharmacia) column, a hydrophobic interaction chromatography (HIC) column, a metal chelate chromatography (IMAC) column, a hydroxy apatite column, or anion exchange or cation exchange columns, thereby removing the Protein A from the mixture. The pH of dissociation can be raised by addition of arginine and/or any composition or agent which reduces (breaks up) or inhibits (prevents) hydrophobic interactions, including, but not limited to ethylene glycol, propylene glycol, ethanol, propanol, methanol, and the like. A higher pH of dissociation allows the removal of rPA at a more neutral pH than dissociation would otherwise occur. Use of a higher pH, e.g., higher than about pH 3.7, also results in less damage, e.g., loss of sulfation or sialation or introduction of Asp-Pro cleavages, to some Fc containing proteins due to lower pH, e.g., pH 3.7.

As used herein, "chromatographic column" generally indicates the numerous types of columns, i.e., columns containing numerous types of substrates, that may be employed in the present invention. Thus, the phrase "chromatographic column" includes, but is not limited to, a Q column, e.g., a Q SEPHAROSE™ Fast Flow (Amersham Pharmacia) column, a hydrophobic interaction chromatography (HIC) column, a metal chelate chromatography (IMAC) column, a hydroxy apatite column, an anion exchange column, or a cation exchange column.

Preferred pH conditions for dissociation of Protein A and Fc containing molecules include pH ranges of 3.7–6.0, 4.0–6.0, 4.5–6.0, 5.0–6.0, 5.0–5.7, 5.2–5.7, and 5.5–5.7. Preferred pH conditions for dissociation of Protein A and Fc containing molecules include conditions at pH of 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, and 6.0. Particularly preferred conditions for dissociation of Protein A and Fc containing molecules is pH of less than 6.0. Also particularly preferred conditions for dissociation of Protein A and Fc containing molecules is pH of 5.0.

Preferred compositions or agents which reduce (break up) or inhibit (prevent) hydrophobic interactions, include, but are not limited to ethylene glycol, propylene glycol, ethanol, propanol, methanol, and the like. Particularly preferred is ethylene glycol for use in dissociating Protein A and Fc containing molecules. Compositions or agents which reduce (break up) or inhibit (prevent) hydrophobic interactions may be used at any concentration which successfully increases the pH sufficiently to allow separation of the Protein A/Fc containing molecule complex using a chromatographic column, including, for example, ranges of concentrations of, e.g., ethylene glycol between 10%–50%, 10–40%, 20%–40%, and 20%–30%. Preferred concentrations of compositions or agents which reduce (break up) or inhibit (prevent) hydrophobic interactions e.g., ethylene glycol include 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, and 50%. Particularly preferred for dissociation of Fc containing compounds, e.g., rPSGL-Ig and Protein A is ethylene glycol at a concentration of 50%.

In one embodiment, an IMAC column may be used for separation of Fc containing molecules, e.g., rPSGL-Ig, from Protein A when used at a pH sufficient to remove a substantial amount of Protein A. In a preferred embodiment, Protein A and Fc containing molecules are dissociated using an IMAC column at pH conditions of between 5.0 and 5.7, preferably pH of 5.0, when a buffer containing 50% ethylene glycol is used to raise the pH of dissociation. In a particularly preferred embodiment, an IMAC column is washed with a buffer containing 50% ethylene glycol, 1M NaCl, and 20 mM Na Acetate, at a pH of about 5.0, to dissociate the rPA from the bound Fc containing molecules, e.g., rPSGL-1, thereby removing a significant portion of the rPA from the Fc containing molecules by using an IMAC column.

In another embodiment, a HIC column may be used for separation of Fc containing molecules, e.g., rPSGL-Ig, from Protein A when used at a pH sufficient to remove a substantial amount of Protein A. In a preferred embodiment, Protein A and Fc containing molecules are dissociated using a HIC column at pH conditions of between 4.1 and 4.5, preferably pH of 4.1, when a buffer containing arginine is used. The HIC column may be run at pH 4.1 with a acv wash at pH 4.1 immediately prior, both in 500 mM arginine, or the HIC column may be eluted at pH 4.1 with 500 mM arginine, but not washed prior to the addition of arginine, to remove Protein A from the Protein A/Fc containing molecule complex.

In a further embodiment, a Q column may be used for separation of Fc containing molecules, e.g., rPSGL-1g, from Protein A when run at a pH sufficient to remove a substantial amount of Protein A. In a preferred embodiment, the Q column is washed in pH conditions of between about 5.5 and 5.7, preferably at 5.5. In a preferred embodiment, 50% ethylene glycol is used to raise the pH of dissociation to allow the use of the Q column to dissociate Protein A from Fc containing molecules, e.g., rPSGL-1g.

As used herein, the term "removal of a substantial amount" of Protein A refers to the removal of 10%–20%, 20%–30%, 30%–40%, 40%–50%, 50%–60%, 60%–70%, 70%–80%, 50%–90%, or preferably, 90%–100% of Protein A from Protein A/Fc containing molecule complexes. Preferably, 10%, 20%, 30%, 40%, 50%, 60%, 70%, 80%, 90% or 100% of Protein A is removed.

As used herein, removal of Protein A such that the Fc containing molecules are substantially free of Protein A refers to the removal of 10%–20%, 20%–30%, 30%–40%, 40%–50%, 50%–60%, 60%–70%, 70%–80%, 50%–90%, or preferably, 90%–100% of Protein A from Protein A/Fc containing molecule complexes, e.g., in a mixture. Preferably, 10%, 20%, 30%, 40%, 50%, 60%, 70%, 80%, 90% or 100% of Protein A is removed.

In a preferred embodiment, the sulfated protein is PSGL-1, for example, PSGL-1 comprising the amino acid set forth in U.S. Pat. No. 5,827,817, the contents of which are incorporated herein by reference, or an active portion thereof. The complete amino acid sequence of the PSGL-1 protein (i.e., the mature peptide plus the leader sequence) is characterized by the amino acid sequence set forth in U.S. Pat. No. 5,827,817 from amino acid 1 to amino acid 402, and set forth herein as SEQ ID NO: 1. Hydrophobicity analysis and comparison with known cleavage patterns predict a signal sequence of 20 to 22 amino acids, i.e., amino acids 1 to 20 or amino acids 1 to 22 of PSGL-1. PSGL-1 contains a PACE (paired basic amino acid converting enzyme) cleavage site (-Arg-Asp-Arg-Arg-) at amino acid residues 38–41. The mature PSGL-1 protein is characterized by the amino acid sequence set forth in SEQ ID NO: 1 from amino acid 42 to amino acid 402. A soluble form of the P-selectin ligand protein is characterized by amino acids 21 to 310 of the amino acid sequence set forth in U.S. Pat. No. 5,827,817. Another soluble form of the mature PSGL-1 protein is characterized by the amino acid sequence set forth in U.S. Pat. No. 5,827,817 from amino acid 42 to amino acid 310. The soluble form of the P-selectin ligand protein is further characterized by being soluble in aqueous solution at room temperature.

Fusion proteins of PSGL-1 (e.g., PSGL-Ig) can be made using art recognized teachings and using the teachings of U.S. Pat. No. 5,827,817, incorporated herein by reference. Fragments of the PSGL-1 protein may be fused to carrier molecules such as immunoglobulins, to increase the valency of P-selectin ligand binding sites. For example, soluble forms of the P-selectin ligand protein such as the fragments from amino acid 42 to amino acid 295 or from amino acid 42 to amino acid 88 of SEQ ID NO:1 may be fused through "linker" sequences to the Fc portion of an immunoglobulin (native sequence or mutated sequences for conferring desirable qualities (such as longer half-life or reduced immunogenicity) to the resulting chimera). For a bivalent form of the P-selectin ligand protein, such a fusion could be to the Fc portion of an IgG molecule (e.g., rPSGL-Ig). Other immunoglobulin isotypes may also be used to generate such fusions. For example, a P-selectin ligand protein-IgM fusion would generate a decavalent form of the P-selectin ligand protein of the invention.

As used herein, the terms "Fc containing protein" or "Fc containing molecule" include any protein which is fused to or includes an Fc portion of an immunoglobulin. An example of an Fc containing protein is rPSGL-Ig.

PSGL-1 is a glycoprotein which may contain one or more of the following terminal carbohydrates:

NeuAcα (2,3) Gal β (1,4) GlcNAc-R
/α(1,3)
Fuc
NeuAcα (2,3) Gal β (1,3) GlcNAc-R
/α(1,4)
Fuc
Gal β (1,4) GlcNAc-R
/αc (1,3)
Fuc
Gal β (1,3) GlcNAc-R
/α(1,4)
Fuc where R=the remainder of the carbohydrate chain, which is covalently attached either directly to the P-selectin ligand protein or to a lipid moiety which is covalently attached to the P-selectin ligand protein. PSGL-1 may additionally be sulfated or otherwise post-translationally modified. As expressed in COS and CHO cells, full length P-selectin ligand protein is a homodimeric protein having an apparent molecular weight of 220 kD as shown by non-reducing SDS-polyacrylamide gel electrophoresis.

The structure of the full-length PSGL-1 includes an extracellular domain (from about amino acid 21 to 310), a transmembrane domain (from about amino acid 311 to 332), and an intracellular, cytoplasmic domain (from about amino acid 333 to 402). The extracellular domain contains three consensus tripeptide sites (Asn-X-Ser/Thr) of potential N-linked glycosylation beginning at Asn residues 65, 111, and 292. The extracellular domain further contains three potential sites of tyrosine sulfation at residues 46, 48, and 51. The region comprised of residues 55–267 contains a high percentage of proline, serine, and threonine including a subdomain of fifteen decameric repeats of the ten amino acid consensus sequence Ala-Thr/Met-Glu-Ala-Gln-Thr-Thr-X-Pro/Leu-AlalThr, wherein X can be either Pro, Ala, Gln, Glu, or Arg. Regions such as these are characteristic of highly O-glycosylated proteins.

Substantial deletions of the PSGL-1 sequence can be made while retaining P-selectin ligand protein activity. For example, PSGL-1 comprising the sequence from amino acid 42 to amino acid 189, the sequence from amino acid 42 to amino acid 118, or the sequence from amino acid 42 to amino acid 89 of SEQ ID NO:1 each retain the P-selectin protein binding activity and the ability to bind to P-selectin. PSGL-1 proteins in which one or more N-linked glycosylation sites (such as those at amino acids 65, 111 and 292) have been changed to other amino acids or deleted also retain P-selectin protein binding activity and the ability to bind E-selectin. P-selectin ligand proteins comprising from amino acid 42 to amino acid 60 (which includes a highly anionic region of the protein from amino acid 45 to amino acid 58) also retain P-selectin ligand protein activity; however, P-selectin ligand proteins limited to such sequence do not bind to E-selectin. Preferably, a P-selectin ligand protein retains at least one (more preferably at least two and most preferably all three) of the tyrosine residues found at amino acids 46, 48 and 51, sulfation of which may contribute to P-selectin ligand protein activity.

This invention is further illustrated by the following examples which should not be construed as limiting. The contents of all references, patents and published patent applications cited throughout this application, are incorporated herein by reference. All references to the amino acid sequence of PSGL-1 are based on the amino acid sequence of PSGL-1 set forth in U.S. Pat. No. 5,827,817 and set forth herein as SEQ ID NO:1.

EXAMPLES

Methods: General methods for purifying proteins are found in Janson, J. C. and L. Ryden (eds.) *Protein Purification: Principles, High Resolution Methods and Applica-*

*tions*. VCH Publishers, Inc. New York (1989), U.S. Pat. No. 5,429,746, entitled Antibody Purification, and U.S. Pat. No. 5,115,101, entitled Removal of Protein from Antibody Preparations, the contents of which are incorporated herein by reference.

Example 1

Purification of Recombinant PSGL-Ig Fusion Protein—Process I

This example describes the purification of a recombinant PSGL-Ig fusion protein by column chromatography.

A soluble P-selectin ligand protein was expressed in CHO cells and the conditioned media was harvested for protein purification. A Q Sepharose™ Fast Flow (Amersham Pharmacia) column with an 8 cm bed depth was prepared according to the manufacturer's instructions. The column capacity for PSGL in conditioned media is approximately 1 mg PSGL/ml resin.

Anion exchange chromatography was performed as follows. Microfiltered CHO conditioned media was loaded onto the column at approximately pH 7, conductivity below 20 mS/cm. The column was washed with 20 mM histidine, 400 mM NaCl, pH 6.5 to remove hyposulfated rPSGL-1g, e.g., 4 or less sulfations. The loading and washing steps were performed at 3.5 cm/minute. The column was eluted at pH 6.5 with 1M NaCl, 20 mM histidine, pH 6.5 at <1.11 cm/minute. The pH of this step could be between pH 4 and 8, but is preferably pH 6.5. The eluted peak contains PSGL-Ig, DNA, and histones as well as other contaminates. The Q column binds DNA, and the histones are attached to the DNA. The PSGL elution (caused by raising the salt concentration) coincides with the DNA elution. The purity of PSGL-Ig is >80%. Only 50% of the DNA is removed by this step.

Under these conditions, hypersulfated rPSGL-Ig molecules, e.g., five or six sulfations, are preferentially purified. Active rPSGL-Ig ideally has five or six sulfations on the N-terminal tyrosines.

The eluent from the anion exchange column was further purified using a hydrophobic interaction chromatography (HIC) column as follows.

A Phenyl Toyopearl 650C column (Rohm and Haas) with a 9 cm bed depth was prepared according to the manufacturer's instructions. The capacity of the HIC column is approximately 3.5 mg PSGL/mL resin. The column was equilibrated in 1.2M ammonium sulfate, 20 mM Tris, pH 7.4 at <1.3 cm/minute. The eluent from the Q Sepharose column was adjusted to 1.2M ammonium sulfate, 20 mM Tris, pH 7.4 by adding 3M ammonium sulfate, 50 mM Tris, pH 7.4, and loaded onto the HIC. Alternatively, the load could be done in 4M NaCl rather than 1.2M Ammonium sulfate. The column was washed with 1.2M ammonium sulfate, 20 mM Tris pH 7.4. Both the loading and washing steps were performed at a rate of approximately 1.3 cm/minute. The HIC column was eluted with 0.48M ammonium sulfate, 20 mM Tris, pH 7.4 at 0.65 cm/minute. Under these conditions, the HIC column removes primarily H2A and H2B histones which do not bind DNA as tightly as H3 and H4 histones. H2 histones appear in the wash fraction, and the peak contains H3 and H4 histones, and some H2 histones. In addition, a large plurality of the DNA stays on the histones and elutes in the peak. The product is >95% pure of contaminating proteins, and 85% of the DNA is removed by this step.

The eluent from the HIC column was further purified using a metal chelate chromatography (IMAC) column as follows.

An IMAC Copper (II) column on Fractogel Chelate (M) (E. Merck) was prepared according to the manufacturer's instructions. The IMAC column had a bed depth 6.47.2 cm, and a capacity of approximately 6.6 mg PSGL/mL resin.

The column was equilibrated with 50 mM potassium phosphate (KPO4), 2.0M NaCl, 2 mM imidazole, pH 7 for 5 cv at <5 cm/minute. The eluent from the HIC column was adjusted to 2 mM imidazole, 50 mM KPO4, pH 7 200 mM NaCl and loaded onto the IMAC column. The column was first washed with equilibration buffer, and then washed with 40 mM MES, 1 M NaCl, 5 mM imidazole, pH 6.6 at <5 cm/minute. This low salt concentration does not break up the histone/DNA complex on the IMAC column. The column was eluted with 40 mM MES, IM NaCl, 35 mM imidazole pH 6.6. The IMAC column removes primarily H3 and H4 histones. H3 and H4 histones, and some H2, are in the strip, although some H3 and H2 histones are found in the IMAC peak. The resulting product is >99.9% pure of contaminating proteins, and this step removes 95% of the DNA. Overall, there is approximately 2.5 LRV of DNA clearance from this whole process.

This process allowed DNA to be carried through the entire process train, as the DNA bound directly to the Q column. In the Q step the DNA also bound to histones (e.g., H2A, H2B, H3, and 114) which are naturally occurring DNA binding proteins which are present in our load to the Q column. On the Q column, therefore, there was a sandwich, in which the DNA bound to the Q column and the histones bound to the DNA. In the subsequent steps, the sandwich was reversed, as DNA does not bind to the HIC or the IMAC column directly. Instead, the histones bound to the HIC or IMAC column, and the DNA bound to the histones. When the histones elute from the HIC or IMAC, they carry the DNA contamination with them. Poor DNA removal due to DNA/protein interactions may be often encountered in protein purification, especially in the case of highly anionic target proteins, and especially where these anionic proteins are eluted from an anion exchange column.

Example 2

Purification of Recombinant PSGL-Ig Fusion Protein—PROCESS II

This example describes the purification of a recombinant PSGL-Ig fusion protein (rPSGL-1g) by column chromatography, including the step of dissociating the contaminating histone/DNA complexes with either salt or an alcohol, thereby increasing the purity of the PSGL-Ig proteins.

An anion exchange chromatography step on Q Sepharose was performed as described in Example 1.

The eluent from the anion exchange column was further purified using a hydrophobic interaction chromatography (HIC) column as follows. A Phenyl Toyopearl 650C column (Rohm and Haas) with a 9 cm bed depth was prepared according to the manufacturer's instructions, and equilibrated in 1.2M ammonium sulfate, 20 mM Tris, pH 7.4. The pH of this step could be between 6–8, but is preferably pH 7.4.

The Q peak was adjusted to 1.2M ammonium sulfate, 20 mM Tris, pH 7.4 by adding 3M ammonium sulfate, 50 mM Tris pH 7.4 and loaded onto the column. Alternatively, the load could be done in 4M NaCl rather than 1.2M ammonium sulfate. The column was washed with 1.2M Ammonium Sulfate, 20 mM Tris pH 7.4, followed by washing with 4M NaCl, 20 mM Tris, pH 7.4. Washing with 4M NaCl removes 90% (or 1 $\log_{10}$ removal or 1 LRV) of the DNA from the column. Alternatively, one could wash with 5% isopropanol and 1.2M Ammonium Sulfate. This removes 99.9% of the DNA from the column ("3 $\log_{10}$ removal", or 3 LRV). Alternatively one could wash with 5% ethanol and 1.2M Ammonium Sulfate. This removes 99.9% of the DNA from the column ("3 $\log_{10}$ removal", or 3 LRV). Alternatively, one could wash with 5% ethanol and 4M NaCl. This removes 99.9% of the DNA from the column ("3 $\log_{10}$ removal", or 3 LRV). Alternatively one could wash with 5% isopropanol and 4M NaCl. This removes 99.9% of the DNA from the column ("3 logo removal", or 3 LRV). The loading and washing steps were performed at a rate of approximately 1.3 cm/minute. The column was then eluted with 0.48M Ammonium Sulfate, 20 mM Tris, pH 7.4 at a rate of 0.65 cm/minute.

As before, this HIC with these conditions removes primarily H2A and H2B histones, which do not bind DNA as tightly as the H3 and H4 histones. H2 histones appear in the wash. The peak contains H3 and H4, with some H2 histones. However, we have found that by washing with higher salt concentrations, the DNA/histone interaction can be broken up. Thus by washing with, for instance, 4M NaCl rather than 1.2M ammonium sulfate, the DNA breaks off from the histone, and comes off in the wash. Under these conditions, a large plurality of the DNA comes off in the wash, and the histones still elute in the peak. This HIC step could alternatively be run after the IMAC step (see below). This could result in 99.9% more DNA being removed (3 LRV).

The eluent from the HIC column was further purified using a metal chelate chromatography (IMAC) column as follows.

An IMAC Copper (II) column on Fractogel Chelate (M) (E. Merck) was prepared according to the manufacturer's instructions. The IMAC column had a bed depth 6.4–7.2 cm, and a capacity of approximately 6.6 mg PSGL/mL resin. The pH of this step can be between 4.8 and 8, but is preferably pH 6.6.

The column was equilibrated with 50 mM potassium phosphate (KPO4), 2.0M NaCl, 2 mM imidazole, pH 7 for 5 cv at <5 cm/minute. Alternatively, the column can be equilibrated at 200 mM NaCl rather than 2M NaCl. The eluent from the HIC column was adjusted to 2 mM imidazole, 50 mM KPO4, pH 7, 200 mM NaCl and loaded onto the IMAC column. The load can alternatively be run at 200 mM NaCl rather than 2M NaCl.

The column was first washed with equilibration buffer, and then washed with 40 mM MES, 2M NaCl, 5 mM Imidazole, pH 6.6 at ≦5 cm/minute. The column was eluted with 40 mM MES, 1M NaCl, 35 mM imidazole pH 6.6. The IMAC column removes primarily H3 and H4 histones. These histones, and some H2 histones, are in the strip. Some H3 and H2 histones are also found in the IMAC peak.

This step removes 90% more DNA than the process I step of Example 1 (1 LRV) using either the high salt load or the high salt wash. The novelty of this step is to load with 2M NaCl or to wash with 2M NaCl to remove the DNA from the histones/DNA complex. The histones stick to the IMAC column, and the DNA sticks to the histones. Since the DNA binds better to the H3/H4 complex than to the H3/H2 or to simply the H2 complex, removing the H3/H4 complex as soon in the process as possible would be beneficial. Thus running the HIC after the IMAC has shown that more DNA clearance can be achieved (99.9% more clearance or 3 LRV). Therefore putting the IMAC as early in the process as possible could conceivably result in a further reduction of DNA. IMAC as the first step, however, would require an ultrafiltration/diafiltration to remove small molecular weight amino acids and other amine containing groups from the load.

Example 3

Purification of Recombinant PSGL-Ig Fusion Protein—Process III

This example describes an alternative method for the purification of a recombinant PSGL-Ig fusion protein, e.g., rPSGL-Ig, by column chromatography. In contrast to the purification scheme described in Example 1, this process uses an affinity step as the first purification step. The affinity purification step uses rProtein A (also referred to herein as rPA) which binds the Fc portion of the rPSGL-Ig chimera. The rPSGL-Ig is eluted from the rProtein A column at low pH, in this case pH of 3.7. The rProtein A step gives better clearance if the column is washed with 1M NaCl after loading. This concentration of salt is higher than that typically used (usually about 150 mM NaCl), and thus is novel. The clearance of DNA from this step goes from 4 $\log_{10}$ removal value (LRV) to 6 LRV with the addition of this salt step. This represents a 100 fold increase in removal of DNA.

The rProtein A step does not appear to bind histones, and gives good DNA clearance. Thus, histones are not noticeably present in the steps following the rProtein A step. However, since the rProtein A leaches from the rProtein A column, the subsequent steps are performed to remove the rProtein A. A novel method for removing the leached Protein A is to load the Protein A eluate directly on the Q column, either at neutral or at low pH, or to wash the Q column at low pH. Q columns are not normally run at low pH, especially not pH 4. Thus the capture of the rPSGL-Ig directly from the Protein A eluate or the washing of the Q column at low pH, or a combination thereof, is novel. Since the rPSGL-Ig and the rProtein A are at low pH, a large plurality of the rPSGL-Ig is not bound to the leached rProtein A. As a result, the rProtein A does not bind to the Q column, but is found in the Q flow through. This is also novel. Thus, the Q column is being used to remove rProtein A. This novel method can be used to purify highly anionic proteins. A Protein A Fast Flow column (Arnersham Pharmacia) with a bed depth of 6–10 cm is prepared according to the manufacturer's instructions. The column capacity is approximately 1 mg/mL to 6 mg/mL. The column is equilibrated with 20 mM Tris, 200 mM NaCl, pH 7.2 to 8, preferably pH 7.4. Microfiltered conditioned media is loaded onto the column between pH 7 and pH 8, preferably pH 7.4, at approximately 30–300 cm/hour, preferably 150 cm/hour. The column is washed with 20 mM Tris, 200 mM NaCl, pH 7 to 8, preferably pH 7.4, and eluted with 20 mM citrate, pH 3 to 4, preferably pH 3.7, at 50–300 cm/hour. The purity is >95% for proteins, and >99% of the DNA is removed by this step.

The eluent from the rProtein A column is further purified on a Q Sepharose™ Fast Flow column (Amersham Pharmacia) with an 8 cm bed depth. The capacity of the Q Sepharose column for PSGL at pH 3.6 to 4.0, preferably about pH 3.8, after the rProtein A step is approximately >6 mg PSGL/mL resin.

The rProtein A peak is loaded directly onto the Q Sepharose column without adjusting the pH, or the peak is neutralized prior to loading onto the Q Sepharose column. In either case, the column is washed with 200 mM NaCl and 20 mM citrate at pH 3.5 to 4, preferably about pH 3.8, to remove residual Protein A. Both methods remove leached Protein A, hyposulfated rPSGL-Ig, N-terminally clipped rPSGL-Ig, and pro-rPSGL-Ig (a precursor species to rPSGL-Ig that does not have enzymatic cleavage of the N-terminus). Following the pH 3.5 to 4 wash, the column could be washed with 20 mM Histidine, 400 mM NaCl, pH 6.5 to remove hyposulfated rPSGL-Ig. Hyposulfated rPSGL-Ig molecules have 4 or less sulfations, whereas active rPSGL-Ig ideally has 5 or 6 sulfations on the N-terminal tyrosines. The column loading and washing steps are performed at a rate of 3.5 cm/minute. The column is eluted at pH 6.5 with 1 M NaCl, 20 mM histidine, pH 6.5. Alternatively, one could elute at pH 3.5 to 4.0 preferably about 3.8 in 500 mM NaCl, 20 mM citrate at <1.1 cm/minute. Proteins represent <2% of the peak.

Alternatively, the leached rProtein A can be removed through raising the pH of dissociation of the Protein A/rPSGL-Ig complex. By raising the pH of dissociation, the Fc containing compound, e.g., rPSGL-Ig, can be more easily separated and removed from the Protein A through the use of a chromatographic column, such as, for example, a Q column, e.g., a Q Sepharose™ Fast Flow (Amersham Pharmacia) column, a hydrophobic interaction chromatography (HIC) column, a metal chelate chromatography (IMAC) column, a hydroxy apatite, anion exchange or cation exchange columns. The pH of dissociation can be raised through use of arginine and/or any other composition which breaks up or prevents hydrophobic interactions thereby raising the pH of dissociation, e.g., ethylene glycol, propylene glycol, ethanol, propanol, methanol, and the like. A higher pH of dissociation allows the removal of rPA at a more normal pH than dissociation would otherwise occur. Use of a higher pH, e.g., higher than about pH 3.7, also results in less damage, e.g., loss of sulfation or sialation or Asp-Pro cleavages, to some Fc containing proteins, e.g., rPSGL-Ig, due to lower pH, e.g., pH 3.7.

Previously, Q columns could not be used for dissociation of rPA from Fc containing proteins (other than Fc containing proteins which are highly anionic), because the pH was generally too low to allow binding of the Fc molecule or the rProtein A to the Q column. Raising the pH of dissociation by, for example, use of arginine and/or ethylene glycol, the pH of dissociation is high enough to allow the use of the Q column for Fc containing molecules under dissociation conditions, including those molecules that are not highly anionic.

Also, previously, IMAC columns could not be used under dissociation conditions, e.g., low pH, again because the Fc containing molecule and the rPA would not remain bound to the IMAC under the normally low pH necessary for the dissociation to occur. Through raising the pH of dissociation by, for example, use of ethylene glycol, the Fc containing protein remains bound to the IMAC column, such that the IMAC column may be used to remove rProtein A.

A HIC column can also be used for removal of rPA from Fc containing molecules at a more normal pH than dissociation would normally occur through raising the pH of dissociation, e.g., by use of arginine and/or ethylene glycol.

Dissociation of rPA and rPSGL-Ig Under IMAC Conditions

The following example describes the characterization of appropriate conditions for removal of rProtein A from rPSGL-Ig using the IMAC column, the HIC column, and the Q column. To develop an rPA removal step for the IMAC column which will remove the rProtein A while the rPSGL-Ig is absorbed onto the IMAC column, conditions must be developed that do not contain any chelating agents, e.g., citrate, or amino acids, e.g., arginine, and must have a relatively high salt concentration to minimize ionic interactions with both the IMAC surface and the rPSGL-Ig surface. Arginine was used in this experiment to explore the possible utility of arginine with the Q column or the HIC column for removal of Protein A.

In order to characterize the dissociation of rPSGL-Ig and rProtein A, a rProtein A column, as described above, was prepared. The rProtein A column was equilibrated with 20 mM tris pH 7.8, 200 mM NaCl. rPSGL-Ig was loaded onto the rPA column. 5M NaCl was added to raise conductivity to 25–30 mS/cm, and the column was titrated with tris HCL or tris base to pH 7.8. The column was washed for 4 cv with equilibration buffer. The elution conditions tested include the following:

Elution 1: 50% ethylene glycol (EG), 200 mM NaCl, 20 mM Na Acetate pH of about 5.7;

Elution 2: 50% EG, 200 mM NaCl, 20 mM Na Acetate pH of about 5.7, and 500 mM arginine;

Elution 3: 50% EG, 1M NaCl, 20 mM Na Acetate, pH of about 5.0; and

Elution 4: 50% EG; 1M NaCl, 20 mM Na Acetate, pH of about 5.0, and 500 mM arginine.

All elutions are 5 cv at 2 mL/min. A final elution was carried out with 20 mM citrate, pH about 2.7.

Results showed that the rPSGL-Ig/rProtein A complex can be broken up with Elution 2, e.g., with a pH around 5.7, and is also broken up with Elution 3, e.g., with a pH around 5.0. The IMAC column could not be used with Elution 2 because of the addition of arginine. Results indicated that 3 cv of Elution 3 (50% EG, 1M NaCl, 20 mM Na Acetate, pH of about 5.0), when applied to an IMAC column, could dissociate the rPA from the bound rPSGL-1 and remove a significant portion of the rPA from the rPSGL-1 process train.

Results also indicate that roughly 20% of the rPA would come off of rPSGL-Ig in a 2 cv wash with Elution 2 (50% EG, 200 mM NaCl, 20 mM Na Acetate, pH of about 5.7, and 500 mM arginine) if PSGL-Ig was bound to another resin, e.g., a Q column or a HIC column. A Q column can be used for removal of Protein A by increasing the pH of dissociation with arginine and, for example, a composition or agent which breaks up hydrophobic interactions, such as, for example, ethylene glycol (EG). For example, the Q column is washed at a pH of about between 5.0 and pH 5.7 with, for example, 200 mM NaCl, 50% ethylene glycol, and 20 mM Na Acetate and 500 mM arginine. A HIC column may also be used for the removal of Protein A with an increased pH of dissociation.

A pH gradient with 50% EG, 1M NaCl on a rProtein A column with PSGL was used to determine the maximum pH that can be used by IMAC for removal of Protein A from rPSGL-Ig. A rProtein A column was prepared as described above and a gradient was tested from pH 5.7 to pH 5.0.

Results indicated that the rPSGL-Ig/rProtein A aggregate can be nearly completely separated at pH 5.3 with 50% ethylene glycol and 1M NaCl, 20 mM Na Acetate. The rPSGL-Ig/rProtein A aggregate can be partially broken up at pH 5.0 with 50% EG and 1M NaCl, 20 mM Na Acetate. rPSGL-Ig can be eluted from the rPA column at pH values as high as 5.5, and can elute relatively well at pH 5.3 in 50% EG, and optionally, 1M NaCl, although the high NaCl concentration is not necessary for the elution. NaCl at a concentration of amount 50–200 mM would be optimal.

Elution at the higher pH compares favorably with the elution at pH 3.7, where the rPSGL-Ig may lose sulfation, sialation, and asp-pro cleavages may occur, which are accelerated at low pH.

Dissociation of rPA and rPSGL-Ig Under HIC Conditions and Column Conditions

To determine the dissociation properties of rPSGL-Ig and rPA in HIC elution conditions and Q column wash conditions, a pH gradient from pH 6 to pH 4 over 20 cv in 20 mM citrate, 500 mM arginine, and 500 mM ammonium sulfate was run to closely mimic the HIC elution conditions. HIC elution conditions are about 0.5M ammonium sulfate.

A rProtein A column was prepared as described above. The column was first equilibrated with 20 mM Tris pH 7.8, 200 mM NaCl. The column was loaded with rPSGLIg, and titrated with tris HCL or tris base to pH 7.8, and washed for 4 cv with equilibration buffer. The gradient was run from 20 mM citrate, 500 mM arginine, and 500 mM ammonium sulfate pH 6 to 20 cv in 20 mM citrate, 500 mM arginine, and 500 mM ammonium sulfate pH 4.

Results indicated that the rPrA/rPSGL-Ig association can be broken up at about pH 4.2 with 500 mM arginine, 0.5M ammonium sulfate, and 20 mM citrate, in contrast to a pH of about 3.7 without the arginine. These results indicate that arginine can strongly affect the dissociation properties of rPSGL-Ig and rPrA. Running a HIC column at about pH 4.1 removes the rPA from the process stream, allowing the rPSGL-Ig to elute rPA free. The HIC column may be run at pH 4.1 with a acv wash at pH 4.1 immediately prior, both in 500 nM arginine. Alternatively, eluting the HIC column at pH 4.1 with 500 mM arginine, but not washing prior to the arginine may also reduce rPA.

An ethylene glycol gradient was run from 0% to 50% over 20 cv in 20 mM acetate, 500 mM arginine, and 500 mM ammonium sulfate. Results indicate that most of the rPS-GLIg is completely dissociated from the PrA at 30% ethylene glycol, pH 4.7, and 500 mM arginine.

Moreover, 2 LRV of rPA can be affected by eluting the rPSGL-Ig in 500 mM arginine, 400 mM ammonium sulfate, pH 4.1, after washing the HIC column with 500 mM arginine, 1.2M ammonium sulfate, pH 4.1.

A further experiment was conducted to investigate whether the addition of arginine and increasing the pH changes the elution conditions of rPSGL-Ig on the HIC column and better resolves the rPSGL-Ig from the rPA on the HIC column with a load containing rPA.

Results indicated that 1.1 LRV of rPA was affected with elution conditions at pH 4.1, 0.9 LRV was affected with elution conditions at pH 4.3, and 0.7 LRV was affected with elution conditions at pH 4.5.

A Q column can also be used to separate the rProtein A/rPSGL-Ig complex through the addition of a composition or agent which acts to separate hydrophobic interactions, e.g., ethylene glycol, at a concentration sufficient to raise the pH to a level which allows the Fc containing molecule to bind to the column may be used to separate the rProtein A with a Q column. For example, a pH of between about 5.5 and 5.7, preferably about 5.5T may be used.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for dissociating Fc-containing molecules from complexes of Protein A/Fc-containing molecules in a mixture comprising the step of contacting the mixture with a hydrophobic interaction column chromatography substrate under pH conditions between about 4.1 and about 4.5, wherein the pH conditions are established by the addition of arginine, or arginine in combination with another agent that reduces or inhibits hydrophobic interactions, to the mixture prior to adding the mixture to the column chromatography substrate, after adding the mixture to the column chromatography substrate, or both prior to and after adding the mixture to the column chromatography substrate, such that the majority of Protein A binds to the column chromatography substrate and the majority of Fc-containing molecules does not bind to the column chromatography substrate.

2. The method of claim 1, wherein the other agent that reduces or inhibits hydrophobic interactions is selected from the group consisting of ethylene glycol, propylene glycol, ethanol, propanol, and methanol.

3. The method of claim 2, wherein the other agent that reduces or inhibits hydrophobic interactions is ethylene glycol.

4. The method of claim 1, further comprising the step of washing the column chromatography substrate with a buffer containing arginine such that Fc-containing molecules are removed from the column chromatography substrate and Protein A remains bound to the column chromatography substrate.

5. The method of claim 4, further comprising the step of eluting the Fc-containing molecules from the column chromatography substrate such that the Fc-containing molecules are substantially free from Protein A.

6. The method of claim 1, wherein the pH is about 4.1.

7. The method of claim 1, wherein the Fc-containing molecule is rPSGL-Ig.

8. A method for dissociating Fc-containing molecules from complexes of Protein A/Fc-containing molecules in a mixture comprising the step of contacting the mixture with a metal chelate column chromatography substrate under pH conditions between about 5.0 and about 5.7, wherein the pH conditions are established by the addition of an agent that reduces or inhibits hydrophobic interactions to to the mixture prior to adding the mixture to the column chromatography substrate, after adding the mixture to the column chromatography substrate, or both prior to and after adding the mixture to the column chromatography substrate, such that the majority of Fc-containing molecules binds to the column chromatography substrate and the majority of Protein A does not bind to the column chromatography substrate.

9. The method of claim 8, wherein the agent that reduces or inhibits hydrophobic interactions is selected from the group consisting of ethylene glycol, propylene glycol, ethanol, propanol, and methanol.

10. The method of claim 9, wherein the agent that reduces or inhibits hydrophobic interactions is ethylene glycol.

11. The method of claim 8, further comprising the step of washing the column chromatography substrate with a buffer comprising about 50% ethylene glycol such that Protein A is removed from the column chromatography substrate and Fc-containing molecules remain bound to the column chromatography substrate.

12. The method of claim 11, further comprising the step of eluting the Fc-containing molecules from the column chromatography substrate such that the Fc-containing molecules are substantially free from Protein A.

13. The method of claim 8, wherein the pH is about 5.0.

14. The method of claim 8, wherein the Fc-containing molecule is rPSGL-Ig.

15. A method for dissociating Fc-containing molecules from complexes of Protein A/Fc-containing molecules in a mixture comprising the step of contacting the mixture with a Q column chromatography substrate under pH conditions between about 5.5 and about 5.7, wherein the pH conditions are established by the addition of arginine and/or another agent that reduces or inhibits hydrophobic interactions to the mixture prior to adding the mixture to the column chromatography substrate, after adding the mixture to the column chromatography substrate, or both prior to and after adding the mixture to the column chromatography substrate, such that the majority of Fc-containing molecules binds to the column chromatography substrate and the majority of Protein A does not bind to the column chromatography substrate.

16. The method of claim 15, wherein the other agent that reduces or inhibits hydrophobic interactions is selected from the group consisting of ethylene glycol, propylene glycol, ethanol, propanol, and methanol.

17. The method of claim 16, wherein the other agent that reduces or inhibits hydrophobic interactions is ethylene glycol.

18. The method of claim 15, further comprising the step of washing the column chromatography substrate with a buffer comprising arginine and/or another agent that reduces or inhibits hydrophobic interactions, such that Protein A is removed from the column chromatography substrate and Fc-containing molecules remain bound to the column chromatography substrate.

19. The method of claim 18, further comprising the step of eluting the Fc-containing molecules from the column chromatography substrate such that the Fc-containing molecules are substantially free from Protein A.

20. The method of claim 15, wherein the pH is about 5.5.

21. The method of claim 15, wherein the Fc-containing molecule is rPSGL-Ig.

* * * * *

UNITED STATES PATENT AND TRADEMARK OFFICE
CERTIFICATE OF CORRECTION

| | | |
|---|---|---|
| PATENT NO. | : 7,223,848 B2 | |
| APPLICATION NO. | : 10/163853 | |
| DATED | : May 29, 2007 | |
| INVENTOR(S) | : Jonathan L. Coffman et al. | |

It is certified that error appears in the above-identified patent and that said Letters Patent is hereby corrected as shown below:

COLUMN 3:

Line 21, "WO 01/2769," should read --WO 01/72769,--; and
Line 28, "removes" should read --remove--.

COLUMN 4:

Line 21, "MAC" should read --IMAC--.

COLUMN 8:

Line 29, "Pro/Leu-AlalThr," should read --Pro/Leu-Ala/Thr,--.

COLUMN 9:

Line 29, "<1.11" should read --<1.1--.

COLUMN 10:

Line 9, "(KPO4)," should read --$(KPO_4)$,--; and
Line 11, "KPO4," should read --$KPO_4$,--.

COLUMN 11:

Line 42, "(KPO4)," should read --$(KPO_4)$,--; and
Line 46, "KPO4," should read --$KPO_4$,--.

COLUMN 12:

Line 42, "flow through." should read --flowthrough.--; and
Line 61, ">6" should read --$\geq 6$--.

UNITED STATES PATENT AND TRADEMARK OFFICE
CERTIFICATE OF CORRECTION

PATENT NO. : 7,223,848 B2
APPLICATION NO. : 10/163853
DATED : May 29, 2007
INVENTOR(S) : Jonathan L. Coffman et al.

It is certified that error appears in the above-identified patent and that said Letters Patent is hereby corrected as shown below:

<u>COLUMN 15</u>:

Line 15, "rPSGLIg," should read --rPSGL-Ig,--.

<u>COLUMN 16</u>:

Line 2, "GLIg" should read --GL-Ig--;
    Line 4, "affected" should read --effected--;
    Line 14, "affected" should read --effected--;
    Line 15, "affected" should read --effected--; and
    Line 16, "affected" should read --effected--;

<u>COLUMN 19</u>:

Line 7, "to to" should read --to--.

Signed and Sealed this

Sixteenth Day of September, 2008

JON W. DUDAS
*Director of the United States Patent and Trademark Office*